United States Patent [19]

Fox et al.

[11] 4,450,310

[45] May 22, 1984

[54] CONVERSION OF METHANE TO OLEFINS AND HYDROGEN

[75] Inventors: Joseph R. Fox, Solon; Benedict S. Curatolo, Maple Heights; Frederick A. Pesa, Aurora, all of Ohio

[73] Assignee: The Standard Oil Company, Cleveland, Ohio

[21] Appl. No.: 471,970

[22] Filed: Mar. 4, 1983

[51] Int. Cl.$^3$ .............................................. C07C 3/44
[52] U.S. Cl. .................... 585/400; 585/500; 585/516; 585/700; 585/832; 585/943; 502/340; 502/341; 502/349
[58] Field of Search ............... 585/516, 654, 832, 943, 585/400, 500, 700, 658; 502/340, 344, 349, 305

[56] References Cited

U.S. PATENT DOCUMENTS

| | | | |
|---|---|---|---|
| 1,905,520 | 4/1933 | Steigerwald | 585/943 |
| 1,995,136 | 3/1935 | Winkler et al. | 585/500 |
| 2,022,279 | 11/1935 | Feiler | 585/943 |
| 2,061,598 | 11/1936 | Smith et al. | 585/943 |
| 4,066,704 | 1/1978 | Harris et al. | 585/658 |
| 4,239,658 | 12/1980 | Mitchell et al. | 585/500 |

FOREIGN PATENT DOCUMENTS

255829 5/1926 United Kingdom ................ 585/943
258608 9/1926 United Kingdom ................ 585/943

OTHER PUBLICATIONS

Keller et al., J. Catalysis, 73, 9–19 (1982).
Kemball, et al., Catalysis, vol. 4, 129–140 (1980) The Royal Society of Chemistry (London).

*Primary Examiner*—Delbert E. Gantz
*Assistant Examiner*—A. Pal
*Attorney, Agent, or Firm*—Joseph G. Curatolo; Larry W. Evans

[57] ABSTRACT

A methane conversion process is provided for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

21 Claims, No Drawings

CONVERSION OF METHANE TO OLEFINS AND HYDROGEN

BACKGROUND OF THE INVENTION

The present invention is directed to a process for the production of olefins and hydrogen from methane. In particular, the present invention provides a process for the production of ethylene, propylene and hydrogen from methane in the absence of steam or oxygen.

Olefins such as ehtylene and propylene are major chemical feedstocks. In 1981, nearly 29 billion pounds of ethylene and 14 billion pounds of propylene were produced in the United States. Ethylene is used in the production of plastics, antifreeze, fibers and solvents, while propylene finds its major uses in plastics and fibers. About 75 percent of the ethylene produced is made by the steam cracking of ethane and propane derived from natural gas (which hydrocarbons comprise less than about 12 percent of natural gas).

U.S. production of hydrogen in 1981 amounted to about 100 billion cubic feet, excluding amounts vented and used as fuel and amounts produced in petroleum refineries for captive use. Hydrogen is used as both a chemical feed and a fuel, and is generally produced by steam reforming of hydrocarbons, especially natural gas, from water gas shift reactions, from catalytic reforming of petroleum stocks and by electrolysis. It has been reported that hydrogen can be formed by the decomposition of methane over iron or nickel catalysts. This process results in the formation of coke on the catalyst, which ultimately destroys the activity of the catalyst.

U.S. Pat. No. 2,020,671 discloses the production of oxygenated organic compounds by reaction of methane or ethane and steam at temperatures of 200°–700° C. in the presence of catalysts selected from alkaline earth metals or any of the metals of groups IV, V, VI, VII and VIII of the periodic table, in addition to aluminum, magnesium and zinc.

U.S. Pat. No. 2,859,258 discloses the production of ethylene from methane in the presence of oxygen containing metal compounds of the second, third and fourth groups of the periodic table, such as aluminum oxide, magnesium aluminum silicate and magnesium aluminum molybdate.

U.S. Pat. Nos. 4,172,810; 4,205,194 and 4,239,658 disclose the production of hydrocarbons including ethylene, benzene, ethane, propane and the like, in the presence of a catalyst-reagent composition which comprises
   (1) a group VIII noble metal having an atomic number of 45 or greater, nickel, or a group Ib noble metal having an atomic number of 47 or greater,
   (2) a group VIb metal oxide which is capable of being reduced to a lower oxide, and
   (3) a group IIa metal selected from the group consisting of magnesium and strontium composited with a passivated, spinel-coated refractory support or calcium composited with a passivated, non-zinc containing spinel-coated refractory support.

It is an object of the present invention to provide a process for the production of olefins and hydrogen from methane.

It is a further object of the present invention to provide a process for the production of olefins, particularly ethylene and propylene, as well as hydrogen from methane with low levels of coke production.

SUMMARY OF THE INVENTION

We have found that methane can be converted to higher hydrocarbons, including olefins, particularly ethylene and propylene, and hydrogen in the presence of catalysts consisting essentially of the oxides of beryllium, magnesium, calcium, strontium, barium and mixtures thereof, or consisting essentially of the oxides of such metals together with a promotor metal selected from copper, rhenium, tungsten, zirconium, and rhodium.

We have also found that methane can be converted to higher hydrocarbons, including olefins such as ethylene or propylene, and hydrogen in the presence of a catalyst comprising the mixed oxides of at least one metal selected from lithium, sodium, potassium, rubidium, and cesium and at least one metal selected from beryllium, magnesium, calcium, strontium and barium, optionally promoted with copper, rhenium, tungsten, zirconium, and rhodium. The process of the present invention permits the upgrading of methane in the absence of air and steam.

The process of the present invention permits the production of olefins and hydrogen without the deactivating coke formation upon the catalyst which is characteristic of prior art processes. The small amount of coke formation which results is not substantially deactivating to the catalyst, and any coke formed on the catalyst may be removed by heating the catalyst in air.

The process of the present invention permits the direct conversion of methane to olefins, particularly ethylene and propylene. Methane, which comprises between 85 and 95 percent of American natural gas, may be used as the feedstock without necessitating separation of the ethane and higher alkane fraction of natural gas which is currently used for cracking to ethylene and propylene. The non-separated natural gas serves as an inexpensive feed stock, as nearly 20 trillion cubic feet are consumed annually in the U.S., approximately 70 percent of which is used as fuel.

In general, the methane conversion process of the present invention includes the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof and a second metal selected from beryllium, magnesium, calcium, strontium, barium, and mixtures thereof, and optionally a promoter metal selected from copper, rhenium, tungsten, zirconium, rhodium, and mixtures thereof.

The present invention further provides a methane conversion process for the production of olefins and hydrogen comprising contacting methane in the absence of oxygen and in the absence of water at a reaction temperature of at least 500° C. with a catalyst consisting essentially of an oxide of a metal selected from beryllium, magnesium, calcium, strontium, barium and mixtures thereof.

The present invention further provides a methane conversion process for the production of olefins and hydrogen comprising contacting methane in the absence of oxygen and in the absence of water at a reaction temperature of at least 500° C. with a catalyst consisting essentially of the mixed oxides of a first metal selected from beryllium, magnesium, calcium, strontium, barium and mixtures thereof, and a second metal selected from copper, rhenium, tungsten, zirconium, rhodium, and mixtures thereof.

DETAILED DESCRIPTION OF THE INVENTION

The catalyst used in the process of the present invention, in one embodiment, consists essentially of the oxides of a metal selected from beryllium, magnesium, calcium, strontium, barium and mixtures thereof. In another embodiment of the invention, the catalyst consists essentially of a first metal selected from beryllium, magnesium, calcium, strontium, barium and mixtures thereof, and a second metal selected from rhodium, copper, rhenium, tungsten, zirconium, and mixtures thereof.

In yet another embodiment of the invention, the catalyst comprises the mixed oxides of a first metal selected from lithium, sodium, potassium, rubidium, cesium and mixtures thereof, a second metal selected from beryllium, magnesium, calcium, strontium, barium and mixtures thereof, and optionally rhodium, copper, rhenium, tungsten, zirconium, and mixtures thereof. In each embodiment of the invention, it is preferred that the catalyst be free of acidic metal oxides such as alumina or silica.

Oxides of the above-listed alkali metal or alkaline earth metal elements may be obtained commercially, or may be prepared by calcination in air of compounds of the metal such as carbonates, hydroxides, halides or salts of organic or inorganic acids. Catalysts which comprise at least one alkali metal and at least one alkaline earth metal may be prepared by impregnating an alkaline earth metal oxide with an aqueous solution of an alkali metal compound such as a hydroxide, and thereafter calcining.

Promoter metal elements may be added to the catalyst by impregnation of the alkaline earth metal oxide or mixed oxides of alkaline earth metal and alkali metal with an aqueous solution of a promoter element containing compound. Suitable promoter element containing compounds include but are not limited to halides, nitrates, oxides, hydroxides, acetates, formates, butyrates and the like.

The molar ratio of alkaline earth metal to alkali metal utilized in the catalyst is generally about 1,000:1 to about 1:1, preferably about 100:1 to about 10:1. The molar ratio of alkaline earth metal to promoter metal utilized in the catalyst, when the promoter metal is present, is generally about 1,000:1 to about 1:1, preferably about 100:1 to about 5:1.

We have found that the basic alkali metal and alkaline earth metal oxides of the present invention contribute to the prevention of significant amounts of coke formation during the reaction process. Catalysts comprising the mixed oxides of alkali metal and alkaline earth metals are particularly basic, and are preferred for the conversion of methane to olefins and hydrogens.

According to the Bronsted concept, the base strength of a solid surface is defined as its proton accepting ability and is quantitatively expressed by the Hammett and Deyrup "H-function" where H-equals $pk_{BH}$-log $C_{BH}/C_{B^-}$, where $pk_{BH}$ is the negative log of the dissociation constant of the protonated form of the base, $C_{BH}$ is the concentration of the protonated form of the base, and $C_{B^-}$ is the concentration of the unprotonated form of the base.

Super bases are defined as those species having H-values greater than about +26 but less than +40, while normal bases have H-values between +7 and about +26. For example, magnesium oxide and calcium oxide, each derived from their respective hydroxides, exhibit H-function values between 18.4 and about 26.5, and are classified as normal bases. Super bases would include the mixed oxides of alkaline earth metals and alkali metals such as magnesium and sodium or calcium and sodium, as well as strontium oxide derived from strontium hydroxide, calcium oxide derived from calcium carbonate and alkaline earth oxides onto which alkali metals have been deposited such as sodium metal, vapor deposited on magnesium oxide. The use of super basic catalysts in the process of the present invention are particularly efficacious in the production of the desired products and the inhibition of coke formation.

The feedstock utilized in the process of the present invention includes methane, derived either from natural gas or as a product of a synthesis gas upgrading process. The methane used in the process of the present invention is substantially free from steam or oxygen (other than as impurities in trace amounts). The feedstock utilized may, however, include inert diluents such as nitrogen, helium, and the noble gases.

The process of the present invention is conducted at a temperature of about 500° C. to about 1500° C., preferably about 700° C. to about 1000° C. The process of the present invention may be carried out at pressures of about 1 to about 100 atmospheres, preferably about 1 to about 20 atmospheres. The methane flow rate may be about 10 to about 1000 cubic centimeters per minute per 10 grams catalyst, preferably about 50 to about 300 cc/minute. Contact times may range from about 0.1 to about 100 seconds.

The process of the present invention may be carried out in conventional fixed bed or fluid bed reactors.

SPECIFIC EMBODIMENTS OF THE INVENTION

The catalysts described in the examples below were tested for the production of olefins and hydrogen from methane by the following procedure. The catalyst was charged to a quartz tube reactor mounted in an electric furnace, either in a horizontal flow system (a 192 cc reactor) with the catalyst spread out along the bottom of the tube in the heating zone, or in a vertical flow system (a 144 cc reactor) with the catalyst held by a quartz frit in the heating zone.

Catalysts were heated to reaction temperature under helium flow. Methane having a purity of 99.8 percent $CH_4$ was introduced into the reactor. Reaction pressure was approximately 1 atmosphere. Effluent gases were analyzed at various times during reaction runs using an analytical gas chromatograph, equipped with both a flame ionization and thermal conductivity detector. Test results are reported as the mole percentage of methane and products in the effluent gas. The majority of the effluent gas was uncoverted methane, suitable for recycle before, or preferably after removal of products.

EXAMPLES 1–19

Reaction runs for Examples 1–19 were conducted utilizing the horizontal flow system, with a methane flow rate of 100–130 cc per minute. Reaction temperature and test results are reported in Table I.

In Examples 1–4, the catalyst utilized was 10 grams magnesium oxide. For Examples 5–8, the catalyst utilized was 10 grams of calcium oxide. As reported in Table I, methane was converted to olefins, particularly ethylene and propylene, and to hydrogen in the presence of the catalyst according to the process of the present invention.

In Comparative Examples 9–11, no catalyst was used in the reaction. Small amounts of hydrogen and olefin were produced during these reaction runs, due either to thermal reactions or possible carbon deposition and catalysis due to the walls of the reactor. A comparison with the previous examples, however, shows the improvement of the process of the present invention in producing olefins and hydrogen.

In Comparative Examples 12 and 13, the catalyst utilized was 10 grams of silicalite (high surface area silica), an acidic oxide material. Considerable coking accompanied the formation of hydrogen, and olefin formation was suppressed.

In Comparative Examples 14 and 15, the catalyst utilized was 10 percent tungsten impregnated on silicalite. Again, considerable coking accompanied production of hydrogen, with little higher hydrocarbon formation.

In Comparative Examples 16 and 17, the catalyst utilized was tungsten metal powder and in Comparative Examples 18 and 19, the catalyst utilized was zirconium metal powder. Reaction results indicate little or no catalytic activity as compared to the blank runs of Comparative Examples 9–11. Whereas these metals alone do not appear catalytic with respect to the methane conversion reaction, these metals promote the activity of the alkaline earth metal oxide catalysts utilized in the process of the present invention, as demonstrated below.

EXAMPLES 20–27

The methane conversion reaction was tested according to the process of the present invention in Examples 20–24 utilizing the horizontal flow system and in Examples 25–27, utilizing the vertical flow system. Temperature, flow rate and results of the reaction runs are reported in Table II.

In Examples 20 and 21 the catalyst utilized was 10 grams of magnesium oxide. In Examples 22–26 the catalyst utilized was 10 grams of calcium oxide. In Comparative Example 27, no catalyst was utilized in the flow system.

EXAMPLES 28–35

The methane conversion reaction was tested according to the process of the present invention utilizing the vertical flow system in Examples 28–35. Reaction temperature was 900° C. The methane flow rate and results of the reaction runs are reported in Table III.

In Examples 28 and 29, the catalyst utilized was 10 grams of calcium oxide. In Comparative Example 30, no catalyst was utilizd in the flow system.

In Examples 31–35, a catalyst comprising the mixed oxides of sodium and calcium was utilized, having been prepared by the following method. 20 grams of calcium oxide was slurried in 116 grams of 50 percent sodium hydroxide (aqueous). The slurry was stirred for two hours, and filtered to yield a white solid. The solid was dried at about 125° C., and calcined in air at 900° C. for about 4.5 hours. In Examples 31 and 32, 10 grams of the catalyst was utilized, and in Examples 33–35, 7.5 grams of the catalyst was utilized.

From the results in Tables I–III, it is demonstrated that the presence of the basic metal oxide catalysts in the reaction according to the present invention increases the per pass conversion of methane to products. It is also demonstrated that the amount of olefins, particularly ethylene and propylene produced from methane increases with the increasing basicity of the metal oxide catalyst used. There is also a trend of decreasing hydrogen production with increasing basicity of the catalyst employed. This trend is consistent with the observed reduced coke formation and increased selectivity toward olefinic products. For example, the percentage of carbon remaining on the silicate catalysts after reaction of 2.25 hours was measured and found to be 5.6 percent. The percentage of carbon remaining on the calcium oxide catalyst having been reacted for 3.5 hours at the same methane flow rate was only 2.3 percent. As demonstrated by the results in Table III, increased activity toward ethylene production is exhibited by catalysts comprising the oxides of alkali metal and alkaline earth metals.

EXAMPLES 36–47

The methane conversion reaction was tested in Examples 36–47 to determine the effect of promoting the alkaline earth metal oxide catalysts with various metal oxides. Temperature, flow rates and reaction results are reported in Table IV. Various metal oxide promoters, when utilized with the catalysts according to the process of the present invention, demonstrated increased activity for olefin production, whereas other metals had either little or detrimental effect. In each of the following examples, two grams of catalyst was utilized in the flow system.

In Examples 36 and 37, calcium oxide was utilized as the catalyst in the flow system.

In Example 38, the catalyst utilized was 2.25 percent rhodium oxide on calcium oxide (by weight of rhodium) prepared by the following method. 1.6 grams rhodium nitrate was dissolved in 20 ml distilled water. 22 grams calcium oxide was impregnated with the rhodium containing solution, was dried and thereafter calcined in air at 900° C.

The catalyst utilized in Examples 39 and 40 was 5 percent rhenium oxide (by weight rhenium) on calcium oxide prepared by the following method. 1.82 grams rhenium chloride was dissolved in about 11 ml distilled water, which was used to impregnate 22 grams calcium oxide. The catalyst was dried at about 110° C. and calcined in air at 900° C.

In Example 41, the catalyst utilized was 5 percent copper oxide (by weight copper) on calcium oxide prepared by the following method. 4.41 grams of cupric nitrate was dissolved in 5 ml distilled water which was used to impregnate 22 grams of calcium oxide. The catalyst was dried at 110° C. and calcined in air at 900° C.

In Examples 42 and 43, the catalyst utilized was 5 percent tungsten oxide (by weight tungsten) on calcium oxide prepared by the following method. 0.77 grams ammonium tungstate was dissolved in 5 ml distilled water. The resulting solution was used to impregnate 10 grams calcium oxide. The catalyst was dried at about 125° C. and calcined in air at 900° C.

In Example 44, the catalyst utilized was 5 percent zirconium oxide (by weight zirconium) on calcium oxide prepared by the following method. 1.89 grams of zirconium acetate was dissolved in 3 ml distilled water to form a solution. 10 grams calcium oxide was impregnated with the solution, was dried at about 125° C. and was calcined in air at 900° C.

As demonstrated in Table IV, rhenium, copper, tungsten, rhodium, and zirconium are promoters for the process of the present invention, promoting olefin production. Vanadium, osmium and palladium are not promoters of the reaction however, these metals causing decreased olefin production, and palladium in particular causing considerable coking with subsequent increased hydrogen production.

In Comparative Example 45, the catalyst utilized was 5 percent vanadium oxide (by weight of vanadium) on calcium oxide prepared by dissolving 1.62 grams vanadium chloride in 5 ml $H_2O$, impregnating 10 grams of calcium oxide with the resulting solution, drying at 125° C. and calcining in air at 900° C.

In Comparative Example 46 the catalyst utilized was 5 percent osmium oxide (by weight osmium) on calcium oxide prepared by dissolving 0.82 osmium chloride in 5 ml distilled water, impregnating 10 grams calcium oxide with the resulting solution, drying at 125° C. and calcining in air at 900° C.

The catalyst utilized in Comparative Example 47 was 5 percent palladium oxide (by weight palladium) on calcium oxide. 3.25 grams of ammonium palladium nitrate was dissolved in 20 ml distilled water, and 22 grams of calcium oxide were impregnated with the resulting solution. The catalyst was dried and calcined at about 900° C. in air.

Thus it should be apparent to those skilled in the art that the subject invention accomplishes the objects set forth above. Although conversions for the system exemplified appear low, increased activity may be exhibited by the use of larger reaction systems, as well as treating the catalyst by methods known in the art to increase surface area. It is to be understood that the subject invention is not to be limited by the examples set forth herein. These have been provided merely to demonstrate operability, and the selection of methods for preparation of the basic oxide catalysts, promoter elements, and reaction conditions can be determined from the total specification disclosure provided without departing from the spirit of the invention herein disclosed and described, the scope of the invention including equivalent embodiments, modifications and variations that fall within the scope of the attached claims.

TABLE I

| Example No. | Catalyst | Temperature °C. | Ethylene | Propylene | Hydrogen | Ethane | Methane |
|---|---|---|---|---|---|---|---|
| 1 | MgO | 800 | 0.292 | 0.02 | — | 0.183 | 96.526 |
| 2 | MgO | 900 | 0.473 | 0.043 | 6.922 | — | 93.156 |
| 3 | MgO | 900 | 0.465 | 0.041 | 7.594 | — | 93.086 |
| 4 | MgO | 900 | 0.541 | 0.043 | 7.048 | — | 93.218 |
| 5 | CaO | 800 | 0.235 | 0.022 | — | 0.159 | 97.769 |
| 6 | CaO | 900 | 0.681 | 0.067 | 6.681 | — | 94.266 |
| 7 | CaO | 900 | 0.566 | 0.058 | 7.176 | — | 94.402 |
| 8 | CaO | 900 | 0.617 | 0.059 | 7.818 | — | 94.705 |
| C9 | — | 800 | — | 0.037 | — | — | |
| C10 | — | 900 | 0.316 | 0.063 | 2.660 | — | |
| C11 | — | 900 | 0.312 | 0.064 | 2.601 | — | |
| C12 | Silicalite | 800 | — | 0.012 | 6.471 | — | 92.744 |
| C13 | Silicalite | 900 | 0.232 | — | 27.487 | — | 71.318 |
| C14 | 10% W/ Silicalite | 800 | — | — | 33.069 | — | 64.941 |
| C15 | 10% W/ Silicalite | 900 | 0.221 | — | 21.556 | — | 80.189 |
| C16 | Tungsten | 800 | — | 0.031 | — | — | |
| C17 | Tungsten | 900 | 0.212 | 0.083 | 1.294 | — | |
| C18 | Zirconium | 800 | 0.122 | 0.025 | — | 0.106 | |
| C19 | Zirconium | 900 | 0.054 | 0.077 | 2.550 | — | |

TABLE II

| Example No. | Catalyst | Temperature °C. | Methane Flow Rate cc/Min | Ethylene | Propylene | Hydrogen | Ethane | Methane |
|---|---|---|---|---|---|---|---|---|
| 20 | MgO | 900 | 260–275 | 0.370 | 0.045 | 3.305 | — | 95.494 |
| 21 | MgO | 900 | 260–275 | 0.397 | 0.044 | 3.064 | 0.177 | 96.647 |
| 22 | CaO | 800 | 260 | 0.184 | 0.017 | — | — | 97.970 |
| 23 | CaO | 900 | 260 | 0.452 | 0.052 | 2.710 | 0.162 | 96.591 |
| 24 | CaO | 900 | 260 | 0.469 | 0.052 | 3.504 | 0.166 | 96.369 |
| 25 | CaO | 900 | 262 | 0.333 | 0.053 | 2.775 | 0.065 | 93.615 |
| 26 | CaO | 900 | 262 | 0.440 | 0.055 | 3.13 | 0.063 | 93.175 |
| C27 | — | 900 | 287 | 0.280 | 0.031 | .8 | — | 98.767 |

TABLE III

| Example No. | Catalyst | Methane Flow Rate cc/Min | Ethylene | Propylene | Hydrogen | Ethane | Methane |
|---|---|---|---|---|---|---|---|
| 28 | CaO | 60 | 0.932 | 0.081 | 11.911 | — | 87.091 |
| 29 | CaO | 60 | 0.862 | 0.077 | 12.057 | — | 86.692 |
| C30 | — | 58 | 0.671 | 0.078 | 7.301 | 0.072* | 92.378 |
| 31 | Na/CaO | 62 | 1.069 | 0.048 | 19.947 | 0.099 | 77.028 |
| 32 | Na/CaO | 62 | 1.387 | 0.062 | 19.406 | — | 79.790 |

TABLE III-continued

| Example No. | Catalyst | Methane Flow Rate cc/Min | Effluent Mole Percentages | | | | |
|---|---|---|---|---|---|---|---|
| | | | Ethylene | Propylene | Hydrogen | Ethane | Methane |
| 33 | Na/CaO | 61 | 1.24 | 0.067 | 17.469 | — | 81.763 |
| 34 | Na/CaO | 61 | 1.286 | 0.070 | 16.119 | 0.154 | 80.82 |
| 35 | Na/CaO | 61 | 1.322 | 0.068 | 17.143 | 0.18 | 81.621 |

*Reaction Temperature 900°C.

TABLE IV

| Example No. | Catalyst (2 grams) | Methane Flow Rate cc/Min | Effluent Mole Percentages | | | | |
|---|---|---|---|---|---|---|---|
| | | | Ethylene | Propylene | Hydrogen | Ethane | Methane |
| 36 | CaO | 266 | 0.251 | 0.034 | 1.3 | — | 99.654 |
| 37 | CaO | 266 | 0.245 | 0.032 | 1.3 | — | 99.206 |
| 38 | 2.25% Rh/CaO | 261 | 0.285 | 0.044 | 1.84 | | 99.673 |
| 39 | 5% Re/CaO | 274 | 0.392 | 0.026 | 1.3 | 0.139* | 98.579 |
| 40 | 5% Re/CaO | 277 | 0.570 | 0.038 | 2.298 | 0.185 | 97.073 |
| 41 | 5% Cu/CaO | 280 | 0.302 | 0.042 | 1.633 | 0.103 | 97.188 |
| 42 | 5% W/CaO | 270 | 0.401 | 0.031 | 3.294 | 0.093 | 95.989 |
| 43 | 5% W/CaO | 270 | 0.415 | 0.034 | 3.671 | 0.092 | 95.782 |
| 44 | 5% Zr/CaO | 270 | 0.352 | 0.036 | 2.785 | 0.15 | 95.122 |
| C45 | 5% V/CaO | 274 | — | 0.018 | 2.445 | — | 98.692 |
| C46 | 5% Os/CaO | 273 | 0.159 | — | 0.961 | 0.058 | 97.598 |
| C47 | 5% Pd/CaO | 280 | — | — | 57.6 | — | |

Reaction Temperature 900° C.

We claim:

1. A process for the conversion of methane comprising contacting methane in the absence of oxygen and in the absence of water at a temperature of at least 500° C. with a catalyst comprising the mixed oxides of a first metal selected from lithium, sodium, potassium, rubidium, cesium and mixtures thereof and a second metal selected from beryllium, magnesium, calcium, strontium, barium and mixtures thereof.

2. A process as in claim 1 wherein said first metal comprises sodium.

3. A process as in claim 1 wherein said second metal comprises calcium.

4. A process as in claim 1 wherein said catalyst additionally comprises an oxide of a promoter metal selected from copper, rhenium, tungsten, zirconium, rhodium, and mixtures thereof.

5. A process as in claim 1 wherein said temperature is between about 700° C. to about 1000° C.

6. A process for the conversion of methane comprising contacting methane in the absence of oxygen and in the absence of water at a reaction temperature of at least 500° C. with a catalyst consisting essentially of an oxide of a metal selected from beryllium, magnesium, calcium, strontium, barium and mixtures thereof.

7. A process as in claim 6 wherein said catalyst contains calcium oxide.

8. A process as in claim 6 wherein said catalyst contains magnesium oxide.

9. A process as in claim 6 wherein said reaction temperature is between about 700° C. and about 1000° C.

10. A process for the conversion of methane comprising contacting methane in the absence of oxygen and in the absence of water at a reaction temperature of at least 500° C. with a catalyst consisting essentially of the mixed oxides of a first metal selected from beryllium, magnesium, calcium, strontium, barium and mixtures thereof, and a second metal selected from copper, rhenium, tungsten, zirconium, rhodium, and mixtures thereof.

11. A process as in claim 10 wherein said reaction temperature is between about 700° C. and about 1000° C.

12. A process as in claim 10 wherein said catalyst contains calcium oxide.

13. A process as in claim 10 wherein said catalyst contains said second metal in an amount of about 2 percent to about 5 percent by weight.

14. A process as in claim 10 wherein said second metal is rhodium.

15. A process as in claim 10 wherein said second metal is rhenium.

16. A process as in claim 10 wherein said second metal is copper.

17. A process as in claim 10 wherein said second metal is zirconium.

18. A process as in claim 10 wherein said second metal is tungsten.

19. A process for the conversion of methane comprising contacting methane in the absence of oxygen and in the absence of water at a temperature of at least 500° C. with a super base solid catalyst having a base strength defined by the equation $$H_- = pK_{BH} - \log C_{BH}/C_{B^-}$$

wherein
  $pK_{BH}$ is the negative log of the dissociation constant of the protonated form of the base,
  $C_{B^-}$ is the concentration of the unprotonated form of the base,
and wherein $H_-$ for the catalyst is between about +26 and +40.

20. A process as in claim 19 wherein said catalyst comprises an alkali metal deposited onto an alkaline earth metal oxide.

21. A process as in claim 20 wherein said catalyst comprises sodium deposited on magnesium oxide.

* * * * *